(12) United States Patent
Wagner-Hattler et al.

(10) Patent No.: US 10,617,648 B2
(45) Date of Patent: *Apr. 14, 2020

(54) DISPERSIBLE DOSAGE FORM

(71) Applicant: Omya International AG, Oftringen (CH)

(72) Inventors: Leonie Wagner-Hattler, Allschwil (CH); Maxim Puchkov, Pfeffingen (CH); Jörg Huwyler, Arlesheim (CH); Tanja Stirnimann, Zofingen (CH); Carolina Diaz Quijano, Oftringen (CH); Joachim Schoelkopf, Oberkulm (CH); Patrick A. C. Gane, Rothrist (CH); Daniel E. Gerard, Basel (CH)

(73) Assignee: Omya International AG, Blue Ash, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/554,235

(22) PCT Filed: Mar. 15, 2016

(86) PCT No.: PCT/EP2016/055590
§ 371 (c)(1),
(2) Date: Aug. 29, 2017

(87) PCT Pub. No.: WO2016/150773
PCT Pub. Date: Sep. 29, 2016

(65) Prior Publication Data
US 2018/0078506 A1 Mar. 22, 2018

Related U.S. Application Data

(60) Provisional application No. 62/203,948, filed on Aug. 12, 2015.

(51) Int. Cl.
*A61K 9/16* (2006.01)
*A61K 9/20* (2006.01)
*C01F 11/18* (2006.01)

(52) U.S. Cl.
CPC .......... *A61K 9/1682* (2013.01); *A61K 9/1605* (2013.01); *A61K 9/1664* (2013.01); *A61K 9/2068* (2013.01); *A61K 9/2095* (2013.01); *C01F 11/185* (2013.01); *C01P 2006/10* (2013.01); *C01P 2006/12* (2013.01); *C01P 2006/14* (2013.01)

(58) Field of Classification Search
None
See application file for complete search history.

(56) References Cited

U.S. PATENT DOCUMENTS

| 3,976,764 | A | 8/1976 | Watanabe et al. |
| 4,451,260 | A | 5/1984 | Mitra |
| 4,627,977 | A | 12/1986 | Gaffar et al. |
| 4,814,179 | A | 3/1989 | Bolton et al. |
| 4,985,459 | A | 1/1991 | Sunshine et al. |
| 5,939,091 | A | 8/1999 | Eoga et al. |
| 2003/0157213 | A1 | 8/2003 | Jenkins |
| 2003/0195220 | A1 | 10/2003 | Murakami et al. |
| 2003/0206993 | A1 | 11/2003 | Gubler |
| 2004/0020410 | A1 | 2/2004 | Gane et al. |
| 2008/0131506 | A1 | 6/2008 | Cavalier et al. |
| 2011/0151014 | A1* | 6/2011 | Thoorens ............. A61K 9/2009 424/499 |
| 2012/0186492 | A1 | 7/2012 | Gane et al. |
| 2015/0166792 | A1 | 6/2015 | Gane et al. |
| 2015/0218382 | A1 | 8/2015 | Gane et al. |
| 2015/0225568 | A1 | 8/2015 | Gane et al. |
| 2015/0231078 | A1 | 8/2015 | Gerard et al. |
| 2015/0283082 | A1 | 10/2015 | Gerard et al. |
| 2017/0290365 | A1* | 10/2017 | Budde .................... C09C 1/022 |
| 2019/0022012 | A1 | 1/2019 | Huwyler et al. |

FOREIGN PATENT DOCUMENTS

| DE | 3527852 A1 | 2/1986 |
| EP | 0338861 A2 | 10/1989 |
| EP | 0717988 A1 | 6/1996 |
| EP | 2070991 A1 | 6/2009 |
| EP | 2264108 A1 | 12/2010 |
| EP | 2264109 A1 | 12/2010 |
| EP | 2719373 A1 | 4/2014 |
| EP | 2719376 A1 | 4/2014 |
| FR | 2787802 A1 | 6/2000 |
| WO | 0039222 A1 | 7/2000 |
| WO | 2004083316 A1 | 9/2004 |
| WO | 2005121257 A2 | 12/2005 |

(Continued)

OTHER PUBLICATIONS

Stirnimann et al. "Functionalized calcium Carbonate as Novel Pharmaceutical Excipient for Preparation of Orally Dispersible Tablets" 2013.*
Stirnimann "Characterization of fucntionalized calcium carbonate as a new pharmaceutical excipeient" Oct. 14, 2014.*
Stirnimann et al. "Compaction of functionalized calcium carbonate, a porous and crystalline microparticulate material with a lamellar surface." International Journal of Pharmaceutics, vol. 466, No. 1-2, May 1, 2014, pp. 266-275.
The International Search Report dated May 17, 2016 for PCT Application No. PCT/EP2016/055590.
The Written Opinion of International Searching Authority dated May 17, 2016 for PCT Application No. PCT/EP2016/055590.
"U.S. Appl. No. 15/534,145, Non Final Office Action dated Aug. 28, 2019", 9 pgs.

(Continued)

Primary Examiner — Jeffrey T. Palenik
Assistant Examiner — Danah Al-Awadi
(74) Attorney, Agent, or Firm — Schwegman Lundberg & Woessner, P.A.

(57) ABSTRACT

The present invention provides for method of improving flowability and loose bulk density of functionalized natural- and/or synthetic calcium carbonate comprising material, to the use of such improved material in ready to use granules and thereof produced dispersible dosage forms.

20 Claims, 2 Drawing Sheets

(56) References Cited

FOREIGN PATENT DOCUMENTS

| WO | 2009074492 A1 | 6/2009 |
|---|---|---|
| WO | 2010037753 A1 | 4/2010 |
| WO | WO-2010146530 A1 | 12/2010 |
| WO | WO-2010146531 A1 | 12/2010 |
| WO | WO-2014001063 A1 | 1/2014 |
| WO | 2014057026 A2 | 4/2014 |
| WO | 2014057038 A1 | 4/2014 |

OTHER PUBLICATIONS

"U.S. Appl. No. 15/534,145, Preliminary Amendment filed Jun. 8, 2017", 8 pgs.

"U.S. Appl. No. 15/534,145, Response filed Mar. 27, 2019 to Restriction Requirement dated Feb. 4, 2019", 6 pgs.

"U.S. Appl. No. 15/534,145, Restriction Requirement dated Feb. 4, 2019", 9 pgs.

"International Application Serial No. PCT/EP2015/080016, International Search Report dated Feb. 22, 2016", 5 pgs.

"International Application Serial No. PCT/EP2015/080016, Written Opinion dated Feb. 22, 2016", 7 pgs.

\* cited by examiner

DISPERSIBLE DOSAGE FORM

CROSS-REFERENCE TO RELATED APPLICATIONS

This is a U.S. national phase of PCT Application No. PCT/EP2016/055590, filed Mar. 15, 2016, which claims priority to European Application No. 15160194.5, filed Mar. 20, 2015 and U.S. Provisional Application No. 62/203,948, filed Aug. 12, 2015.

The present invention relates to a method for producing ready to use granules, to dosage forms comprising such ready to use granules, and the use of such ready to use granules comprising functionalized natural or synthetic calcium carbonate comprising particles, in a variety of applications providing for a simple and fast method or producing simple and fast dispersible dosage forms in an aqueous environment.

In many industries simple and fast dispersible dosage forms in an aqueous environment are required. Such dosage form are mainly manufactured out of powders. Depending on the final use, the carrier material or matrix for such dispersible dosage forms need to be first mixed with the required active ingredient or inactive precursor material and compatible disintegrants need to be found in order to be able to produce a dosage form, which depending on the composition are more or less readily dispersible in an aqueous environment. A frequent problem arising in the production of such dosage form is, that the carrier material or matrices, which are provided in powdered form are not always free flowing material and thus the conveyance, transport and dosage of such material is difficult and sometimes even impossible.

Functionalised natural or synthetic calcium carbonate comprising particles, if not used in wet from, either as a dispersion or suspension, but in dry form is belonging to the material described above which are sometimes difficult to handle.

WO2010/037753 refers to carriers for the controlled release of active agents, comprising surface-reacted natural or synthetic calcium carbonate, one or more active agents, wherein said one or more active agent is associated with said surface-reacted calcium carbonate. It further relates to the preparation of loaded carriers, as well as their use in different applications.

WO2014/057038 refers to an orally fast disintegrating dosage forms comprising functionalized natural or synthetic calcium carbonate, at least one active ingredient and at least one disintegrant, wherein said functionalized natural or synthetic calcium carbonate is a reaction product of natural or synthetic calcium carbonate with carbon dioxide and one or more acids, wherein the carbon dioxide is formed in situ by the acid treatment and/or is supplied from an external source, and wherein the tablet dissolves in less than 20 seconds when introduced into an aqueous environment.

WO 2014/057026 refers to an instantly floating gastroretentive drug formulation comprising at least one functionalized natural and/or synthetic calcium carbonate-comprising material and at least one pharmaceutically active ingredient and at least on formulating aid wherein said functionalized natural and/or synthetic calcium carbonate-comprising material is a reaction product of natural and/or synthetic calcium carbonate with carbon dioxide and one or more acids, wherein the carbon dioxide is formed in situ by the acid treatment and/or is supplied firm an external source.

The unpublished European Patent application 14199037.4 of the present applicant refers to roller compacting of a mixture comprising a functionalized natural- or synthetic calcium carbonate, an active pharmaceutical ingredient and/or inactive precursor, and one or more formulating aids and compacting the roller compacted mixture thus obtained into a pharmaceutical delivery system.

Throughout the present invention and in view of the cited prior art, surface reacted natural or synthetic calcium carbonate is equivalent to functionalized natural and/or synthetic calcium carbonate-comprising material.

All prior art applications use the functionalized natural or synthetic calcium carbonate directly out of the pot, which means that the functionalized natural or synthetic calcium carbonate is used in powdered form.

Powdered material as long as it is handled in lab scale, do not pose any technical problems, as all operations are done manually and are under permanent control. In industrial production however, powders pose quite a challenge when being worked in auto- or semi-automated production lines and/or systems.

However, none of the foregoing documents explicitly mention the compacting of functionalized natural and/or synthetic calcium carbonate-comprising material in order to provide for granules as a starting material which are ready to use for the production of subsequent dosage forms.

Therefore a first aspect of the present invention is related to a method for producing compacted material also known as granules which are a simple and fast dispersible dosage forms in an aqueous environment. Said granules have the advantage of an improved flowability, loose bulk- and tapped bulk-density, compared to the powder they have been made of, and are significantly less or almost non-dusting and thus can be safely manipulated and easily be used in auto- or semi-automated production lines and/or systems.

The method thus for producing a dispersible dosage form in an aqueous environment comprises the steps of:

a) providing a functionalized natural and/or synthetic calcium carbonate-comprising material, which is a reaction product of natural ground or precipitated calcium carbonate with carbon dioxide and one or more acids in an aqueous medium, wherein the carbon dioxide is formed in situ by the acid treatment and/or is supplied from an external source, b) providing at least one disintegrant;

c) optionally providing at least one further formulating aid;

d) mixing the functionalized natural and/or synthetic calcium carbonate-comprising material of step a), the at least one disintegrant of step b) and the optionally at least one further formulating aid of step c); and e) compacting the mixture obtained in step d) by means of a roller compactor at a compaction pressure in the range from 2 to 20 bar into a ribbon; and f) milling the ribbon of step e) into granules.

g) sieving of the granules of step f) by at least one mesh size.

According to one embodiment of the present method, the natural calcium carbonate comprising material is selected from natural ground calcium carbonate containing minerals selected from the group comprising marble, chalk, dolomite, limestone and mixtures thereof; and the synthetic calcium carbonate comprising material is selected from the group comprising precipitated calcium carbonates having aragonitic, vateritic or calcitic mineralogical crystal forms and mixtures thereof.

According to another embodiment of the present method, the functionalised natural and/or synthetic calcium carbonate of step a) has a BET specific surface area of from 20.0 $m^2/g$ to 450.0 $m^2/g$, preferably from 20.0 $m^2/g$ to 250.0 $m^2/g$, more preferably from 30.0 $m^2/g$ to 160.0 $m^2/g$, even more preferably from 40.0 m$^2$/g to 150.0 m$^2$/g, and most preferably from 50.0 m$^2$/g to 140.0 m$^2$/g, measured using nitrogen and the BET method according to ISO 9277; and/or b) comprises particles having a volume median grain diameter d$_{50}$ of from 2.0 to 50.0 μm, preferably from 2.5 to 25.0 μm, more preferably from 2.8 to 20.0 μm, even more preferably from 3.0 to 10.0 μm, and most preferably from 4.0 to 8.0 μm; and/or c) has an intra-particle intruded specific pore volume within the range of 0.10 to 3.35 cm$^3$/g, preferably of 0.25 to 3.30 cm$^3$/g, and most preferably of 0.70 to 3.25 cm$^3$/g, calculated from a mercury intrusion porosimetry measurement.

It should be understood that for the purpose of the present invention the following terms have the following meaning.

For the purpose of the present invention, an "acid" is defined as Brønsted-Lowry acid, that is to say, it is an H3O+ ion provider. An "acid salt" is defined as an H3O+ ion-provider, e.g., a hydrogen-containing salt, which is partially neutralised by an electropositive element. A "salt" is defined as an electrically neutral ionic compound formed from anions and cations.

In accordance with the present invention, pKa is the symbol representing the acid dissociation constant associated with a given ionisable hydrogen in a given acid, and is indicative of the natural degree of dissociation of this hydrogen from this acid at equilibrium in water at a given temperature. Such pKa values may be found in reference textbooks such as Harris, D. C. "Quantitative Chemical Analysis: 3rd Edition", 1991, W.H. Freeman & Co. (USA), ISBN 0-7167-2170-8.

For the purpose of the present invention, a "functionalised natural or synthetic calcium carbonate" is a material comprising calcium carbonate and a water insoluble, at least partially crystalline, non-carbonate calcium salt, preferably, extending from the surface of at least part of the calcium carbonate. The calcium ions forming said at least partially crystalline non-carbonate calcium salt originate largely from the starting calcium carbonate material that also serves to form the functionalized natural and/or synthetic calcium carbonate-comprising material core. Such salts may include OH— anions and/or crystal water.

In the meaning of the present invention "water-insoluble" materials are defined as materials which, when mixed with deionised water and filtered on a filter having a 0.2 μm pore size at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of recovered solid material following evaporation at 95 to 100° C. of 100 g of said liquid filtrate.

"Natural ground calcium carbonate" (GCC) in the meaning of the present invention is a calcium carbonate obtained from natural sources, such as limestone, marble, dolomite, or chalk, and processed through a wet and/or dry treatment such as grinding, screening and/or fractionating, for example, by a cyclone or classifier. Said natural ground calcium carbonate being the base material for the functionalised natural calcium carbonate.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. Said precipitated calcium carbonate being the base for the functionalised synthetic calcium carbonate.

Throughout the present document, the "particle size" of a calcium carbonate and other materials is described by its distribution of particle sizes. The value dx represents the diameter relative to which x % by weight of the particles have diameters less than d$_x$. This means that the d$_{20}$ value is the particle size at which 20 wt.-% of all particles are smaller, and the d$_{75}$ value is the particle size at which 75 wt.-% of all particles are smaller. The d$_{50}$ value is thus the weight median particle size, i.e. 50 wt.-% of all grains are bigger and the remaining 50 wt.-% of grains smaller than this particle size. For the purpose of the present invention the particle size is specified as weight median particle size d$_{50}$ unless indicated otherwise. For determining the weight median particle size d$_{50}$ value a Sedigraph can be used. For the purpose of the present invention, the "particle size" of functionalized natural and/or synthetic calcium carbonate-comprising material is described as volume determined particle size distributions. For determining the volume determined particle size distribution, e.g., the volume median grain diameter (d$_{50}$) or the volume determined top cut particle size (d$_{98}$) of functionalized natural and/or synthetic calcium carbonate-comprising material, a Malvern Mastersizer 2000 can be used. The weight determined particle size distribution may correspond to the volume determined particle size if the density of all the particles is equal.

A "specific surface area" (expressed in m$^2$/g) of a material as used throughout the present document can be determined by the Brunauer Emmett Teller (BET) method with nitrogen as adsorbing gas and by use of a Gemini V instrument from Micromeritics. The method is well known to the skilled person and defined in ISO 9277:1995. Samples are conditioned at 250° C. for a period of 30 min prior to measurement. The total surface area (in m$^2$) of said material can be obtained by multiplication of the specific surface area (in m$^2$/g) and the mass (in g) of the material.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

The "intraparticle intruded specific pore volume" according to the present invention can be calculated from a mercury intrusion porosimetry measurement and describes the measured pore volume that is found inside the pigment particles per unit mass of sample containing the particles. The intruded total specific void volume represents the sum of all the individual pore volumes, which can be intruded by mercury, per unit mass of the sample can be measured by mercury porosimetry using a Micrometrics Autopore IV mercury porosimeter. An exemplary mercury porosimetry experiment entails the evacuation of a porous sample to remove trapped gases, after which the sample is surrounded with mercury. The amount of mercury displaced by the sample allows calculation of the sample's bulk volume, V$_{bulk}$. Pressure is then applied to the mercury so that it intrudes into the sample through pores connected to the external surface. The maximum applied pressure of mercury can be 414 MPa, equivalent to a Laplace throat diameter of 0.004 μm. The data can be corrected using Pore-Comp (P. A. C. Gane et al. "Void Space Structure of Compressible Polymer Spheres and Consolidated Calcium Carbonate Paper-Coating Formulations", Industrial and Engineering Chemistry Research 1996, 35 (5):1753-1764) for mercury and penetrometer effects, and also for sample compression. By taking the first derivative of the cumulative intrusion curves the pore size distributions based on equivalent Laplace diameter, inevitably including the effect of pore-shielding when present, are revealed. The intruded total specific void volume corresponds to the void volume per unit mass of the sample determined by mercury porosimetry.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" though such a limited understanding is always included by the terms "obtained" or "defined" as a preferred embodiment.

According to the present invention it has been found that calcium carbonate, which has been surface treated in a certain way, can be used as excipient in pharmaceutical delivery systems and provides the possibility of efficiently compacting the pharmaceutical delivery systems.

In the following, it is referred to further details of the present invention and especially the foregoing steps of the method for producing a pharmaceutical delivery system.

According to step a) of the instant method, a functionalized natural and/or synthetic calcium carbonate-comprising material is provided, which is a reaction product of natural ground or precipitated calcium carbonate with carbon dioxide and one or more acids in an aqueous medium, wherein the carbon dioxide is formed in situ by the acid treatment and/or is supplied from an external source.

The functionalized natural and/or synthetic calcium carbonate-comprising material used according to the present invention is a reaction product of natural ground or precipitated calcium carbonate with carbon dioxide and at least one acid in an aqueous medium, wherein the carbon dioxide is formed in situ by the acid treatment and/or is supplied from an external source.

The expression "acid treatment" in the meaning of the present invention refers to the reaction of the natural ground or precipitated calcium carbonate and the at least one acid in the aqueous medium. By this reaction carbon dioxide can be formed in-situ in the aqueous medium.

Natural ground calcium carbonate (GCC) is understood to be a naturally occurring form of calcium carbonate, mined from sedimentary rocks such as limestone or chalk, or from metamorphic marble rocks. Calcium carbonate is known to exist mainly as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Natural calcium carbonate is almost exclusively of the calcitic polymorph, which is said to be trigonal-rhombohedral and represents the most stable of the calcium carbonate polymorphs. The term "source" of the calcium carbonate in the meaning of the present invention refers to the naturally occurring mineral material from which the calcium carbonate is obtained. The source of the calcium carbonate may comprise further naturally occurring components such as magnesium carbonate, alumino silicate etc.

According to one embodiment the natural ground calcium carbonate is selected from calcium carbonate containing minerals selected from the group consisting of marble, chalk, dolomite, limestone, and mixtures thereof.

According to one embodiment of the present invention the GCC is obtained by dry grinding. According to another embodiment of the present invention the GCC is obtained by wet grinding and optionally subsequent drying.

In general, the grinding step can be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. It is to be noted that the same grinding methods can be used for dry grinding the calcium carbonate containing mineral material. The wet processed ground calcium carbonate containing mineral material thus obtained may be washed and dewatered by well-known processes, e.g. by flocculation, filtration or forced evaporation prior to drying. The subsequent step of drying may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is selected from the group consisting of precipitated calcium carbonates having aragonitic, vateritic or calcitic mineralogical crystal forms, and mixtures thereof.

In a preferred embodiment, the natural ground or precipitated calcium carbonate is ground prior to the treatment with the at least one acid and carbon dioxide. The grinding step can be carried out with any conventional grinding device such as a grinding mill known to the skilled person.

In a preferred process, the natural ground or precipitated calcium carbonate, either finely divided, such as by grinding, or not, is suspended in water. Preferably, the slurry has a content of natural ground or precipitated calcium carbonate within the range of 1 wt.-% to 80 wt.-%, more preferably 3 wt.-% to 60 wt.-%, and even more preferably 5 wt.-% to 40 wt.-%, based on the weight of the slurry.

According to one embodiment of the present invention, the natural ground or precipitated calcium carbonate has a weight median particle size $d_{50}$ of from 0.1 to 50 µm, preferably from 0.5 to 25 µm, more preferably from 0.8 to 20 µm, even more preferably from 1.0 to 10 µm and most preferably from 1.2 to 8 µm.

In a next step, at least one acid is added to the aqueous suspension containing the natural ground or precipitated calcium carbonate. The at least one acid can be any strong acid, medium-strong acid, or weak acid, or mixtures thereof, generating $H_3O^+$ ions under the preparation conditions. According to the present invention, the at least one acid can also be an acidic salt, generating $H_3O^+$ ions under the preparation conditions.

According to one embodiment, the at least one acid is a strong acid having a $pK_a$ of 0 or less at 20° C. According to another embodiment, the at least one acid is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the acid is preferably selected from $H_2SO_3$, $H_3PO_4$, oxalic acid, or mixtures thereof. According to a preferred embodiment, the least one acid is $H_3PO_4$. The at least one acid can also be an acidic salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one acid can also be a mixture of one or more acids and one or more acidic salts.

According to still another embodiment, the at least one acid is a weak acid having a $pK_a$ value of greater than 2.5 and less than or equal to 7, when measured at 20° C., associated with the ionisation of the first available hydrogen, and having a corresponding anion formed on loss of this first available hydrogen, which is capable of forming water-soluble calcium salts. According to the preferred embodiment, the weak acid has a $pK_a$ value from 2.6 to 5 at 20° C., and more preferably the weak acid is selected from the group consisting of acetic acid, formic acid, propanoic acid, and mixtures thereof.

In case a weak acid is used, after addition of said acid to the aqueous suspension containing the natural ground or precipitated calcium carbonate, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally added. The cation of said water-soluble salt is preferably selected from the group consisting of potassium, sodium, lithium and mixtures thereof. In a more preferred embodiment, said cation is sodium. It is of note that depending on the charge of the anion, more than one of said cations may be present to provide an electrically neutral ionic compound. The anion of said water-soluble salt is preferably selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 15 minutes. It is more preferred to add said salt in one step.

According to one embodiment of the present invention, the at least one acid is selected from the group consisting of hydrochloric acid, sulphuric acid, sulphurous acid, phosphoric acid, citric acid, oxalic acid, acetic acid, formic acid, and mixtures thereof. Preferably the at least one acid is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$ or $Ca^{2+}$, and mixtures thereof, more preferably the at least one acid is selected from the group consisting of hydrochloric acid, sulphuric acid, sulphurous acid, phosphoric acid, oxalic acid, or mixtures thereof, and most preferably, the at least one acid is phosphoric acid.

According to another embodiment of the present invention, the at least one acid is a mixture of one or more acids. For example, the at least one acid is a mixture of phosphoric acid and citric acid. The one or more acids may be added simultaneously or successively.

The at least one acid can be added to the suspension as a concentrated solution or a more diluted solution. According to one embodiment, the molar ratio of the at least one acid to the natural ground or precipitated calcium carbonate is from 0.01 to 0.6, preferably from 0.05 to 0.55, and more preferably from 0.1 to 0.5. As an alternative, it is also possible to add the at least one acid to the water before the natural ground or precipitated calcium carbonate is suspended.

In a next step, the natural ground or precipitated calcium carbonate is treated with carbon dioxide. The carbon dioxide can be formed in situ by the acid treatment and/or can be supplied from an external source. If a strong acid such as sulphuric acid or hydrochloric acid or a medium-strong acid such as phosphoric acid is used for the acid treatment of the natural ground or precipitated calcium carbonate, the carbon dioxide is automatically formed in a sufficient amount to achieve the required molar concentration. Alternatively or additionally, the carbon dioxide can be supplied from an external source.

According to one embodiment, the functionalized natural and/or synthetic calcium carbonate-comprising material is a reaction product of natural ground or precipitated calcium carbonate with carbon dioxide and at least one acid, wherein the carbon dioxide is formed in situ as a result of contacting the at least one acid with the natural ground or precipitated calcium carbonate and/or is supplied from an external source.

Acid treatment and treatment with carbon dioxide can be carried out simultaneously which is the case when a strong or medium-strong acid is used. It is also possible to carry out acid treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the acid treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably from 1:0.05 to 1:5.

In a preferred embodiment, the acid treatment step and/or the carbon dioxide treatment step are repeated at least once, more preferably several times.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing functionalized natural and/or synthetic calcium carbonate-comprising material as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

Further details about the preparation of the functionalized natural and/or synthetic calcium carbonate-comprising material are disclosed in WO 00/39222, WO 2004/083316, WO 2005/121257, WO 2009/074492, EP 2 264 108, EP 2 264 109 and US 2004/0020410.

Similarly, functionalized natural and/or synthetic calcium carbonate-comprising material, is obtained. As can be taken in detail from EP 2 070 991, functionalized synthetic calcium carbonate-comprising material is obtained by contacting precipitated calcium carbonate with $H_3O^+$ ions and with anions being solubilized in an aqueous medium and being capable of forming water-insoluble calcium salts, in an aqueous medium to form a slurry of functionalized synthetic calcium carbonate-comprising material, wherein said functionalized synthetic calcium carbonate-comprising material comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

According to one embodiment of the present invention, the functionalized natural and/or synthetic calcium carbonate-comprising material is obtained by a process comprising the steps of:
a) providing a suspension of natural ground or precipitated calcium carbonate,
b) adding at least one acid having a $pK_a$ value of 0 or less at 20° C. or having a $pK_a$ value from 0 to 2.5 at 20° C. to the suspension of step a), and
c) treating the suspension of step a) with carbon dioxide before, during or after step b).

According to one embodiment, at least one acid having a $pK_a$ value of 0 or less at 20° C. is added in step b) to the suspension of step a). According to another embodiment, at least one acid having a $pK_a$ value from 0 to 2.5 at 20° C. is added in step b) to the suspension of step a).

The carbon dioxide used in step c) can be formed in situ by the acid treatment of step b) and/or can be supplied from an external source.

According to one embodiment of the present invention, the functionalized natural and/or synthetic calcium carbonate-comprising material is obtained by a process comprising the steps of:
A) providing a natural ground or precipitated calcium carbonate,
B) providing at least one water-soluble acid,
C) providing gaseous $CO_2$,
D) contacting said natural ground or precipitated calcium carbonate of step A) with the at least one acid of step B) and with the $CO_2$ of step C),
characterised in that:
i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and
ii) following contacting the at least one acid with natural ground or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

According to one embodiment of the preparation of the functionalized natural and/or synthetic calcium carbonate-comprising material, the natural ground or precipitated calcium carbonate is reacted with the at least one acid and/or the carbon dioxide in the presence of at least one compound selected from the group consisting of silicate, magnesium oxide, citric acid, aluminium sulphate, aluminium nitrate, aluminium chloride, and mixtures thereof. These components can be added to an aqueous suspension comprising the natural ground or precipitated calcium carbonate before adding the at least one acid and/or carbon dioxide.

The functionalized natural and/or synthetic calcium carbonate-comprising material can be kept in suspension. Alternatively, the aqueous suspension described above can be dried.

The functionalized natural and/or synthetic calcium carbonate-comprising material to be used in the present invention preferably is provided in the dried powder form. The subsequent step of drying may be carried out by any method known to the skilled person. For example, the drying can be carried out in a single step such as spray drying, or in at least two steps, e.g. by applying a first heating step to the functionalized natural and/or synthetic calcium carbonate-comprising material in order to reduce the associated moisture content, and applying a second heating step to the functionalized natural and/or synthetic calcium carbonate-comprising material in order to reduce the remaining moisture content.

The term "dry" functionalized natural and/or synthetic calcium carbonate-comprising material is understood to be a functionalized natural and/or synthetic calcium carbonate-comprising material having less than 1.8% by weight of water relative to the functionalized natural and/or synthetic calcium carbonate-comprising material weight. The % water may be determined by heating the functionalized natural and/or synthetic calcium carbonate-comprising material to 105° C. in a drying chamber using the method according to ISO 787-2.

The functionalized natural and/or synthetic calcium carbonate-comprising material to be used in the present invention is provided in dry form. The functionalized natural and/or synthetic calcium carbonate-comprising material is preferably in the form of dust or powder and most preferably in the form of powder.

According to one embodiment of the present invention, the functionalized natural and/or synthetic calcium carbonate-comprising material comprises an insoluble, at least partially crystalline calcium salt of an anion of the at least one acid, which is formed on the surface of the natural ground or precipitated calcium carbonate. According to one embodiment, the insoluble, at least partially crystalline salt of an anion of the at least one acid covers the surface of the natural ground or precipitated calcium carbonate at least partially, preferably completely. Depending on the employed at least one acid, the anion may be sulphate, sulphite, phosphate, citrate, oxalate, acetate and/or formiate.

According to one preferred embodiment, the functionalized natural calcium carbonate-comprising material is a reaction product of natural ground calcium carbonate and at least one acid, preferably phosphoric acid. According to another preferred embodiment, the functionalized natural calcium carbonate-comprising material is a reaction product of natural ground calcium carbonate and phosphoric acid in combination with citric acid.

Furthermore, in a preferred embodiment, the functionalized natural and/or synthetic calcium carbonate-comprising material has a BET specific surface area of from 20.0 $m^2/g$ to 450.0 $m^2/g$, preferably from 20.0 $m^2/g$ to 250.0 $m^2/g$, more preferably from 30.0 $m^2/g$ to 160.0 $m^2/g$, even more preferably from 40.0 $m^2/g$ to 150.0 $m^2/g$, and most preferably from 50.0 $m^2/g$ to 140.0 $m^2/g$, measured using nitrogen and the BET method according to ISO 9277 77.

According to one embodiment, the functionalized natural and/or synthetic calcium carbonate-comprising material comprises particles having a volume median grain diameter $d_{50}$ of from 2.0 to 50.0 μm, preferably from 2.5 to 25.0 μm, more preferably from 2.8 to 20.0 μm, even more preferably from 3.0 to 10.0 μm, and most preferably from 4.0 to 8.0 μm. Preferably, the volume median grain diameter is measured with a Malvern Mastersizer 2000 Laser Diffraction System. The method and the instrument are known to the skilled person and are commonly used to determine grain sizes of fillers and pigments.

Additionally or alternatively, the functionalized natural and/or synthetic calcium carbonate-comprising material comprises particles having a top cut particle size ($d_{98}$) of less than or equal to 40.0 μm, preferably less than or equal to 30.0 μm, more preferably less than or equal to 20.0 μm, still more preferably of less than or equal to 17.0 μm, more preferably of less than or equal to 14.0 μm. Preferably, the functionalized natural and/or synthetic calcium carbonate-comprising material comprises particles having a top cut particle size ($d_{98}$) in the range of from 5.0 to 40 μm, preferably form 6 to 30 μm, more preferably form 7.0 to 20.0 μm, still more preferably of from 8.0 to 17.0 μm, more preferably of from 11.0 to 14.0 μm.

Preferably, the functionalized natural and/or synthetic calcium carbonate-comprising material has an intra-particle intruded specific pore volume within the range of 0.15 to 1.35 $cm^3/g$, preferably of 0.30 to 1.30 $cm^3/g$, and most preferably of 0.40 to 1.25 $cm^3/g$, calculated from mercury intrusion porosimetry measurement as described in the experimental section. The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bimodal. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired specific pore volume of the internal pores alone as the specific pore volume per unit mass. The same principle of subtraction, of course, applies for isolating any of the other pore size regions of interest.

The pore diameter of the functionalized natural and/or synthetic calcium carbonate-comprising material preferably is in a range of from 4 to 500 nm, more preferably in a range of between 20 and 80 nm, especially from 30 to 70 nm, e.g. 50 nm determined by mercury porosimetry measurement.

According to a preferred embodiment the intra- and/or inter particle pores of the functionalized natural and/or synthetic calcium carbonate-comprising material are hollow and, therefore, the functionalized natural and/or synthetic calcium carbonate-comprising material is unloaded. In other words, the functionalized natural and/or synthetic calcium carbonate-comprising material is not used as a carrying agent.

Preferably, the functionalized natural and/or synthetic calcium carbonate-comprising material has inter-particle voids within the range of from 50 vol. % (v/v) to 99 vol. % (v/v), preferably of from 70 vol. % (v/v) to 98 vol. % (v/v), especially of from 80 vol. % (v/v) to 95 vol. % (v/v) calculated from a mercury porosimetry measurement as described in the experimental section.

Additionally or alternatively, the functionalized natural and/or synthetic calcium carbonate-comprising material has core voids within the range of from 1 vol. % (v/v) to 30 vol. % (v/v), preferably of from 5 vol. % (v/v) to 20 vol. % (v/v), especially of from 10 vol. % (v/v) to 15 vol. % (v/v) calculated from a mercury porosimetry measurement as described in the experimental section.

The functionalized natural and/or synthetic calcium carbonate-comprising material may be in the form of dust or powder and preferably in the form of powder.

According to one embodiment the functionalized natural and/or synthetic calcium carbonate-comprising material does not contain nano-scale particles, e.g. particles with at least one dimension less than 200 nm. A "nano-scale particle" in the meaning of the present invention refers to fine particles with at least one dimension less than 200 nm. According to one embodiment of the present invention, the functionalized natural and/or synthetic calcium carbonate-comprising material does not contain particles that have a number based median particle size $d_{50}$ of less than 200 nm. For determining the number based median particle size $d_{50}$ value, a Malvern Zetasizer Nano ZS can be used employing dynamic light scattering to determine the equivalent spherical hydrodynamic Stokes diameter.

According to step b) in order to promote disintegration of the granules a disintegrating agent or disintegrants are commonly used. Such disintegrants are known to the skilled person as well as their mechanisms of action.

There are three major mechanisms and factors affecting tablet disintegration:

Swelling
Porosity and Capillary Action
Deformation
Swelling

Although not all effective disintegrants swell in contact with water, swelling is believed to be a mechanism in which certain disintegrating agents (such as starch) impart a disintegrating effect. By swelling in contact with water, the adhesiveness of other ingredients in a tablet is overcome causing the tablet to fall apart.

Porosity & Capillary Action

Effective disintegrants that do not swell are believed to impart their disintegrating action through porosity and capillary action. Granule porosity provides pathways for the penetration of fluid into the granules. The disintegrant particles, sometimes with low cohesiveness and compressibility, themselves act to enhance porosity and provide these pathways into the granule. Liquid is drawn up into these pathways through capillary action and rupture the interparticulate bonds causing the granule to disintegrate.

Deformation

Starch grains are generally thought to be elastic in nature, meaning that grains that are deformed under pressure will return to their original shape when that pressure is removed. But, with the compression forces involved in roller compaction, these grains are believed to be deformed more permanently and are said to be rich in energy with this energy being released upon exposure to water. In other words, the ability for starch to swell is higher in energy rich starch grains than it is for starch grains that have not been deformed under pressure.

It is believed that no single mechanism is responsible for the action of most disintegrants. But rather, it is most likely the result of inter-relationships between these major mechanisms.

Within the context of the present invention the term disintegrant or disintegrating agent encompass disintegrants exhibiting the above mentioned mechanisms.

The granules according to the present invention comprise at least one disintegrant exhibiting one of the mechanisms described above. Preferably the granules according to the present invention comprise at least one disintegrant selected form the group comprising modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-, hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxpropyl methyl cellulose phtalate, shellac or mixtures thereof.

Examples of suitable disintegrants are: Ac-Di-Sol®, FMC, USA—which is a modified cellulose gum; Kollidon®CL, BASF, Germany—which is an insoluble crosslinked polyvinlypyrrolidone; Vivastar®, JRS, Germany—which is a sodium starch glycolate; MCC Polymorph II (MCC SANAQ Burst®)—Pharmatrans Sanaq AG, Switzerland—which is a stable crystal polymorph type II of Microcrystalline cellulose, MCC SANAQ 102 as standard microcrystalline cellulose (MCC).

It lies within the understanding of the skilled person that the mentioned disintegrants are of mere illustrative character and are not intended to be of limiting character.

The at least one disintegrant is present in the range from about 0.3 wt % to about 10 wt %, preferably from about 0.5 wt % to about 8 wt %, more preferably from about 1 wt % to about 5 wt % based on the weight of functionalized natural and/or synthetic calcium carbonate-comprising material. In a particular embodiment, the disintegrant is present in an amount of 3 wt % to 4 wt % based on the weight of functionalized natural and/or synthetic calcium carbonate-comprising material.

According to a further embodiment of the present method, the optionally at least one formulating aid of step c) is at least one inner-phase lubricant and/or outer-phase lubricant; and is provided in a total amount from about 0.1 wt.-% to about 10.0 wt.-%, preferably from about 0.3 wt.-% to about 5.0 wt %, more preferably from about 0.5 wt.-% to about 2.5 wt.-% based on the total weight of the functionalized natural and/or synthetic calcium carbonate-comprising material of step a).

Said at least one inner-phase lubricant can be selected from the group comprising sorbitan esters of fatty acids and polyoxyethylated hydrogenated castor oil (e.g. the product sold under the trade name CREMOPHOR®), block copolymers of ethylene oxide and propylene oxide (e.g. products sold under trade names PLURONIC® and POLOXAMER), polyoxyethylene fatty alcohol ethers, polyoxyethylene sorbitan fatty acid esters, sorbitan esters of fatty acids and polyoxyethylene steraric acid esters, stearyl alcohol, glycerol dibehenate, sodium stearyl fumarate, glycerol distearate and combinations thereof. Preferably, said at least one inner-phase lubricant is sodium stearyl fumarate.

Said at least one outer-phase lubricant can be selected from the group comprising lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllactylate, magnesium and/or calcium stearate, hydrogenated vegetable oils, stearic acid, sodium lauryl sulphate, magnesium lauryl sulphate, colloidal silica, talc and combinations thereof. Preferably, said at least one outer-phase lubricant is magnesium and/or calcium stearate, more preferably magnesium stearate.

According to a further embodiment of the present method, the optionally at least one formulating aid of step c) may be further selected from polymers, fillers, binders, diluents, lubricants, film forming agents, adhesives, buffers, adsorbents, natural or synthetic scenting agents, natural or synthetic flavouring agents, natural or synthetic coloring agents, natural or synthetic sweeteners, natural or synthetic odour-masking agents, natural or synthetic flavouring- or taste-masking agents, natural and/or synthetic mouthfeel enhancers and/or mixtures thereof.

According to step d) of the instant method, the functionalized natural and/or synthetic calcium carbonate-comprising material of step a), the at least one disintegrant of step b) and the optionally at least one formulating aid of step c) are mixed.

Mixing the functionalized natural and/or synthetic calcium carbonate-comprising material of step a) the at least one disintegrant of step b) and the optionally at least one formulating aid of step c) can be carried out simultaneously or separately in any order to form a mixture.

In one embodiment of the present invention, method step d) is carried out in that the functionalized natural and/or synthetic calcium carbonate-comprising material of step a) is combined simultaneously with the at least one disintegrant of step b) and the at least one formulating aid of step c). For example, method step d) is carried out in that the functionalized natural and/or synthetic calcium carbonate-comprising material of step a) is combined with a blend consisting of the at least one disintegrant of step b) and the optionally at least one formulating aid of step c). That is to say, said at least one disintegrant of step b) and the at least one optionally formulating aid of step c) may be pre-mixed prior to addition to said functionalized natural and/or synthetic calcium carbonate-comprising material of step a).

Preferably, mixing step d) is carried out in that the at least one disintegrant of step b) and the at least one optional formulating aid of step c) are added independently from each other to the functionalized natural and/or synthetic calcium carbonate-comprising material of step a).

For the purposes of the present invention, any suitable mixing means known in the art may be used. However, mixing step d) preferably takes place in a mixer and/or blender, preferably a mixer such as a tumbling mixer.

According to step e) of the present method the mixture obtained in step d) is compacted by means of a roller compacter at a compaction pressure in the range from 2 to 20 bar. The term "roller compacting" refers to a process in which fine powders are forced between two counter rotating rolls and pressed into a solid compact or ribbon.

For the purposes of the present invention, roller compacting can be carried out with any suitable roller compactor known to the skilled person. For example, roller compacting is carried out with a Fitzpatrick® Chilsonator IR220 roller compactor of the Fitzpatrick Company, USA.

It is one requirement of the instant method that method step e) is carried out at a compaction pressure in the range from 2 to 20 bar. Preferably, roller compacting step e) is carried out at a roller compaction pressure in the range from 4 to 15 bar, more preferably in the range from 4 to 10 bar and most preferably in the range from 4 to 7 bar.

Additionally or alternatively, the feed rate and/or the roll speed during roller compacting step is/are adjusted such that a ribbon thickness of from 0.2 to 6 mm, preferably from 0.3 to 3 mm and more preferably from 0.4 to 1 mm is obtained. For example, the feed rate or the roll speed during roller compacting step e) is adjusted such that a ribbon thickness of from 0.4 to 0.8 mm, preferably from 0.5 to 0.7 mm and most preferably of about 0.6 mm is obtained. Alternatively, the feed rate and the roll speed during roller compacting step e) are adjusted such that a ribbon thickness of from 0.4 to 0.8 mm, preferably from 0.5 to 0.7 mm and most preferably of about 0.6 mm is obtained.

According to step f) of the present invention, the roller compacted mixture obtained in the roller compacting step e) is subjected to a milling step. Milling is carried out with any conventional mill known to the skilled person. For example, milling is carried out with a FitzMill® from the Fitzpatrick Company, USA.

According to step g) of the present invention the granules of step f) are submitted to at least on sieving step g) on at least one mesh size. Such sieving can be carried out with any conventional sieving means known to the skilled person. The sieving can be carried out using one or more mesh sizes. Suitable mesh sizes are, but not limited to mesh sizes in the order of 180 µm, 250 µm, 355 µm, 500 µm and 710 µm.

The sieved mixture thus has a grain size of from 180 to 710 µm obtained by sieving on different mesh sizes, preferably by sieving with mesh sizes in the order of 180 µm, 250 µm, 355 µm, 500 µm and 710 µm. More preferably, by sieving with mesh sizes in the order of 180 µm, 250 µm, 355 µm, 500 µm and 710 µm and combining the sieved mixtures such that grain sizes of less than 180 µm and more than 710 µm are excluded.

For example, sieving is carried out with a Vibrating sieve tower of Vibro Retsch, Switzerland.

It lies within the understanding of the present invention that other mesh sizes and combination of other mesh sized lie within the spirit of the present invention.

A further aspect of the present invention is that the granules of the present invention obtained in step g) have an improved flowability compared to the functionalized natural and/or synthetic calcium carbonate-comprising material of step a), as shown in table 1. Further to this, the granules obtained in step g) are ready to use granules in further methods for producing dispersible dosage forms. Such dosage forms are comprising tablets, mini-tables, pellets, capsules, jelly beans or chewing gums comprising these granules.

Further to this the granules and the above mentioned dosage forms can be comprised in pharmaceutical, nutraceutical, cosmetic, home, and personal care products.

TABLE 1

Granule properties. Both formulations, the granules compressed at 10 bar (and combined sieved fractions from 180 µm-710 µm) and the powder were composed of 97 wt.-% FCC and 3 wt.-w % of disintegrant (Ac-Di-Sol ®, FMC, USA)

| Formulation | Flowability (g/s) | | | Loose bulk density ($g/cm^3$) | Tapped bulk density ($g/cm^3$) | Specific surface ($m^2/g$) |
| --- | --- | --- | --- | --- | --- | --- |
| | 5 mm | 7 mm | 9 mm | | | |
| Granules 10 bar | 1.36 ± 0.00 | 3.39 ± 0.00 | 5.75 ± 0.03 | 0.65 | 0.70 | 38.2 |
| Powder | No flow | No flow | No flow | 0.13 | 0.25 | 48.5 |

Values for flowability are means ± standard deviation (SD) of n = 3 experiments.

According to a further aspect of the present invention, the granules of the present invention obtained in step g) have a loose bulk density in the range of 0.65 g/cm$^3$, and a tapped density in the range of 0.70 g/cm$^3$, when roller compacted at 10 bar, milled and sieved to a fraction having a particle size from 180 μm to 710 μm.

According to a further aspect of the present invention, the method comprising the steps a) to g) may further comprise a step b1) of providing at least one active ingredient or inactive precursor or both between step b), and step c) or step d).

Within the context of the present invention, an active ingredient encompasses also inactive pharmaceutical and biological precursors which will be activated at a later stage.

The granules of the present invention may thus still further comprise at least one active ingredient, preferably the active ingredient is selected from the group comprising pharmaceutically active ingredients, inactive pharmaceutical precursors, biologically active ingredients, inactive biological precursors or combinations thereof.

The activation of such inactive precursors is known to the skilled person and commonly in use, e.g. activation in the stomach and/or gastro-intestinal pathway—such as acidic activation, tryptic, chimotryptic or pepsinogenic cleavage.

It lies within the understanding of the skilled person that the mentioned activation methods are of mere illustrative character and are not intended to be of limiting character.

According to yet another embodiment of the present method, the at least one pharmaceutically active agent or pharmaceutically inactive precursor thereof is selected from the group comprising pharmaceutically active agent or pharmaceutically inactive precursor of synthetic origin, semi-synthetic origin, natural origin and combinations thereof.

According to another aspect of the present invention, the method comprising the steps a) to g) may further comprise a step d1) of providing at least one lubricant after step d) and mixing the mixture of step d) with the at least one lubricant of step d1) in a mixing step d2) prior to the compacting step e).

According to another aspect of the present invention, the method comprising the steps a) to g) including the step b1) as mentioned above may further comprise the steps d1) and d2) as mentioned above.

According to yet a further aspect of the present invention, the method comprising the steps a) to g) or the method comprising the steps a) to g) and further comprising the steps d1) and d2) as mentioned above, may further comprise the step h) of providing at least one active ingredient and/or inactive precursor and optionally a step i) of providing further additives, and mixing the granules of step g) with the at least one active ingredient and/or inactive precursor of step h) and the optionally provided further additives of step i).

According to still another aspect of the present invention, the method comprising the steps a) to g) or the method comprising the steps a) to g) including the step b1) as mentioned above or the method of steps a) to g) including the steps d1) and d2) as mentioned above or the method comprising the steps a) to g) including the step b1) and further including the steps d1) and d2) or the method comprising the steps a) to g) or the method comprising the steps a) to g) and further comprising the steps d1) and d2) as mentioned above, further comprising the step h) and optionally step i) as mentioned above may further comprise a final step j) of tableting the material obtained in the last step of the method comprising the steps a) to g) or the method comprising the steps a) to g) including the step b1) as mentioned above or the method of steps a) to g) including the steps d1) and d2) as mentioned above or the method comprising the steps a) to g) including the step b1) and further including the steps d1) and d2) or the method comprising the steps a) to f) or the method comprising the steps a) to g) and further comprising the steps d1) and d2) as mentioned above, further comprising the step h) and optionally step i) as mentioned above.

Still another aspect of the present invention refers to tablets obtained by the methods described herein after the tableting step j). The tableting step j) is carried out at a compressive pressure in the range from 0.5 to 500 MPa. Preferably, the tableting step i) is carried out at a compressive pressure in the range from 1 to 400 MPa, and most preferably in the range from 10 to 400 MPa. For example, tableting step j) is carried out at a compressive pressure in the range from 50 to 300 MPa, and most preferably in the range from 50 to 200 MPa or from 100 to 200 MPa.

For example, tableting is carried out with a tablet press such as a Styl'One 105 ml tablet press from Medel'Pharm, France. The properties of the tablets are summarized in table 2.

TABLE 2

| Tablet properties. | | | | | |
|---|---|---|---|---|---|
| Mean compressive pressure (MPa) | Weights (mg) | Height (mm) | Diameter (mm) | Hardness (N) | Disintegration time (s) |
| 49.85 ± 0.00 | 482.8 ± 1.0 | 3.86 ± 0.00 | 11.36 ± 0.00 | 64 | 9.32 |
| 65.32 ± 0.08 | 504.0 ± 0.7 | 3.82 ± 0.00 | 11.36 ± 0.00 | 98 | 10.73 |
| 74.63 ± 0.06 | 522.1 ± 0.1 | 3.83 ± 0.01 | 11.36 ± 0.00 | 129 | 8.45 |
| 86.57 ± 0.02 | 542.0 ± 1.5 | 3.84 ± 0.01 | 11.36 ± 0.00 | 154 | 9.34 |
| 99.07 ± 0.72 | 563.2 ± 2.2 | 3.86 ± 0.01 | 11.36 ± 0.00 | 188 | 10.30 |
| 113.40 ± 0.20 | 581.6 ± 0.5 | 3.86 ± 0.00 | 11.36 ± 0.00 | 225 | 13.05 |

The volume for all the compacted tablets was kept constant (V = 390 ± 2 mm$^3$).

Values are means ± standard deviation (SD) of n = 3 experiments with the exception of hardness and disintegration time (n = 1).

The tablets having hardness from 60 to 230 N, and disintegration times from 9 to 14 seconds, as shown in table 2.

It lies with in the spirit of the present invention that the tableting step j) can also be replaced by other compressing or compacting steps resulting in other dosage form than tablet. Such other dosage forms comprise but are not limited to, mini-tablets, pellets, capsules, jelly beans or chewing gums.

A first embodiment of the present invention is thus the method for producing a dispersible dosage form in an aqueous environment comprises the steps of:
a) providing a functionalized natural and/or synthetic calcium carbonate-comprising material, which is a reaction product of natural ground or precipitated calcium carbonate with carbon dioxide and one or more acids in an aqueous medium, wherein the carbon dioxide is formed in situ by the acid treatment and/or is supplied from an external source,
b) providing at least one disintegrant;
c) optionally providing at least one further formulating aid;
d) mixing the functionalized natural and/or synthetic calcium carbonate-comprising material of step a), the at least one disintegrant of step b) and the optionally at least one further formulating aid of step c); and
e) compacting the mixture obtained in step d) by means of a roller compactor at a compaction pressure in the range from 2 to 20 bar into a ribbon; and
f) milling the ribbon of step e) into granules.
g) sieving of the granules of step f) by at least one mesh size.

A second embodiment, being the first embodiment, further comprising a step b1) of providing at least one active ingredient or inactive precursor or both between step b), and step c) or step d).

A third embodiment, being the first embodiment, further comprising a step d1) of providing at least one lubricant after step d) and mixing the mixture of step d) with the at least one lubricant of step d1) in a mixing step d2) prior to the compacting step e).

A fourth embodiment, being the second embodiment, further comprising a step d1) of providing at least one lubricant after step d) and mixing the mixture of step d) with the at least one lubricant of step d1) in a mixing step d2) prior to the compacting step e). A fifth embodiment, being the first or third embodiment, further comprising a step h) of providing at least one active ingredient and/or inactive precursor and optionally a step i) of providing further additives, and mixing the granules of step g) with the at least one active ingredient and/or inactive precursor of step h) and the optionally provided further additives of step i).

A sixth embodiment, being any one of the first to fifth embodiment, further comprising a final step j) of tableting the material obtained in the last step in any of the first to fifth embodiments.

A further embodiment being any one of the first to fifth method further comprising a sieving step g) wherein the granules of the grinding step f) are sieved on different mesh sizes, preferably with mesh sizes of 180 μm, 250 μm, 355 μm, 500 μm, and 710 μm. The methods as described above, further comprising a tableting step h)

Yet another aspect of the present invention is the use of functionalized natural and/or synthetic calcium carbonate-comprising material in the method of producing a dispersible dosage form, comprising the steps of:
a) providing a functionalized natural and/or synthetic calcium carbonate-comprising material, which is a reaction product of natural ground or precipitated calcium carbonate with carbon dioxide and one or more acids in an aqueous medium, wherein the carbon dioxide is formed in situ by the acid treatment and/or is supplied from an external source,
b) providing at least one disintegrant;
c) optionally providing at least one further formulating aid;
d) mixing the functionalized natural and/or synthetic calcium carbonate-comprising material of step a), the at least one disintegrant of step b) and the optionally at least one further formulating aid of step c); and
e) compacting the mixture obtained in step d) by means of a roller compactor at a compaction pressure in the range from 2 to 20 bar into a ribbon; and
f) grinding the ribbon of step e) into granules.
g) sieving of the granules of step f) by at least one mesh size.

A further aspect of the present invention is the use of functionalized natural and/or synthetic calcium carbonate-comprising material in the method comprising the steps a) to f) further comprise a step b1) of providing at least one active ingredient or inactive precursor or both between step b), and step c) or step d).

A still further aspect of the present invention is the use of functionalized natural and/or synthetic calcium carbonate-comprising material in a method, the method comprising the steps a) to f) further comprising a step d1) of providing at least one lubricant after step d) and mixing the mixture of step d) with the at least one lubricant of step d1) in a mixing step d2) prior to the compacting step e).

Yet still a further aspect of the present invention is the use of functionalized natural and/or synthetic calcium carbonate-comprising material in a method, the method comprising the steps a) to g) including the step b1) as mentioned above and further comprising the steps d1) and d2) as mentioned above.

According to yet a still further aspect of the present invention is the use of functionalized natural and/or synthetic calcium carbonate-comprising material in a method, the method comprising the steps a) to g) or the method comprising the steps a) to g) and further comprising the steps d1) and d2) as mentioned above, and further comprising the step h) of providing at least one active ingredient and/or inactive precursor and optionally a step i) of providing further additives, and mixing the granules of step g) with the at least one active ingredient and/or inactive precursor of step h) and the optionally provided further additives of step i).

According to still another aspect of the present invention is the use of functionalized natural and/or synthetic calcium carbonate-comprising material in a method, the method comprising the steps a) to g) or the method comprising the steps a) to g) including the step b1) as mentioned above or the method of steps a) to g) including the steps d1) and d2) as mentioned above or the method comprising the steps a) to g) including the step b1) and further including the steps d1) and d2) or the method comprising the steps a) to g) or the method comprising the steps a) to g) and further comprising the steps d1) and d2) as mentioned above, and comprising the step h) and optionally step i) as mentioned above further comprising a final step j) of tableting the material obtained in the last step of the method comprising the steps a) to g) or the method comprising the steps a) to g) including the step b1) as mentioned above or the method of steps a) to g) including the steps d1) and d2) as mentioned above or the method comprising the steps a) to g) including the step b1) and further including the steps d1) and d2) or the method comprising the steps a) to g) or the method comprising the steps a) to g) and further comprising the steps d1) and d2)

as mentioned above, further comprising the step h) and optionally step i) as mentioned above.

According to still another aspect of the present invention is the use of functionalized natural and/or synthetic calcium carbonate-comprising material in any method described above, further comprising a sieving step g) wherein the granules of the grinding step f) are sieved on different mesh sizes, preferably with mesh sizes of 180 μm, 250 μm, 355 μm, 500 μm, and 710 μm.

According to a further embodiment the at least one lubricant of step d1), is at least one inner-phase lubricant and/or outer-phase lubricant; and is provided in a total amount from about 0.1 wt.-% to about 10.0 wt.-%, preferably from about 0.3 wt.-% to about 5.0 wt %, more preferably from about 0.5 wt.-% to about 2.5 wt.-% based on the total weight of the functionalized natural and/or synthetic calcium carbonate-comprising material of step a).

Within the context of the present invention, the active ingredient or inactive precursor as mentioned in the methods as described above comprising the step g) an active ingredient encompasses also inactive pharmaceutical and biological precursors which will be activated at a later stage.

The granules of the present invention may thus still further comprise at least one active ingredient selected from the group comprising pharmaceutically active ingredients, inactive pharmaceutical precursors, biologically active ingredients, inactive biological precursors or combinations thereof.

The activation of such inactive precursors is known to the skilled person and commonly in use, e.g. activation in the stomach and/or gastro-intestinal pathway—such as acidic activation, tryptic, chimotryptic or pepsinogenic cleavage.

It lies within the understanding of the skilled person that the mentioned activation methods are of mere illustrative character and are not intended to be of limiting character.

According to yet another embodiment of the present method, the at least one pharmaceutically active agent or pharmaceutically inactive precursor thereof is selected from the group comprising pharmaceutically active agent or pharmaceutically inactive precursor of synthetic origin, semi-synthetic origin, natural origin and combinations thereof.

Also within the meaning of the present invention, the further additives optionally provided in step h) in methods as mentioned above include but are not limited to the disintegrant mentioned above, fillers, binders, diluents, lubricants, film forming agents, adhesives, buffers, adsorbents, natural or synthetic scenting agents, natural or synthetic flavouring agents, natural or synthetic colouring agents, natural or synthetic sweeteners, natural or synthetic odour-masking agents, natural or synthetic flavouring or taste-masking agents, natural or synthetic mouthfeel enhancers and/or mixtures thereof. Suitable natural or synthetic scenting agents include one or more volatized chemical compounds, generally at a very low concentration, that humans or animals perceive by the sense of olfaction.

Suitable natural or synthetic flavouring agents or taste masking agents include but are not limited to mints, such as peppermint, menthol, vanilla, cinnamon, various fruit flavours, both individual or mixed, essential oils such as thymol, eucalyptol, menthol, and methyl salicylate, allylpyrazine, methoxypyrazines, 2-isobutyl-3 methoxypyrazine, acetyl-L-pyrazines, 2-acetoxy pyrazine, aldehydes, alcohols, esters, ketones, pyrazines, phenolics, terpenoids and mixtures thereof.

The flavouring agents are generally utilized in amounts that will vary depending upon the individual flavour, and may, for example, range in amount of about 0.5% to about 4% by weight of the final composition.

Suitable natural or synthetic colouring agents include, but are not limited to, titanium dioxide, flavone dyes, isoquinoline dyes, polyene colorants, pyran colorants, naphthochinone dyes, chinone and anthrachinone dyes, chromene dyes, benzophyrone dyes as well as indigoid dyes and indole colorants. Examples thereof are caramel colouring, annatto, chlorophyllin, cochineal, betanin, turmeric, saffron, paprika, lycopene, pandan and butterfly pea.

Suitable natural or synthetic sweeteners or taste masking agents include but are not limited to xylose, ribose, glucose, mannose, galactose, fructose, dextrose, sucrose, sugar, maltose, steviol glycosides, partially hydrolyzed starch, or corn syrup solid, and sugar alcohols such as sorbitol, xylitol, mannitol, and mixtures thereof; water soluble artificial sweeteners such as the soluble saccharin salts, i.e. sodium, or calcium saccharin salts, cyclamate salts, acesulfam-K and the like, and the free acid form of saccharin and aspartame based sweeteners such as L-aspartyl-phenylalanine methyl ester, Alitame® or Neotame®.

In general, the amount of sweetener will vary with the desired amount of sweeteners selected for a particular final composition.

Suitable natural and/or synthetic mouthfeel enhancers in step c) and/or step h) comprise but are not limited to polyethylenoxide (PEO-1NF), provided by Sumitomo Seika, Osaka, Lot. L20141017A, Hydroxylpropylcellulose (L-HPC LH-11), Shin-Etsu, Japan, Lot. 505200, Hydroxypropylethylcellulose (Methocel E15 LV Premium EP), Lot. LD250012N23, Gummi arabicum Pheur, Roth, Germany, Lot. 024208213, or Instant gum AA, Nexira, France or combinations thereof.

97% FCC S02 and 3% AcDiSol was rollercompacted with 10 bar. The ribbons were milled with the Fitzmill hammer mill with the mesh 1729-001 at 300 rpm. The granules were sieved in order to get 2 fractions of particles: 180 μm-500 μm and 500 μm-710 μm. The above mentioned mouthfeel enhancers were added in amounts of: 5% (w/w), 7.5% (w/w) and 10% (w/w).

Three different particle size fractions were investigated: 180-500 μm (yielding mean particle size of 340 μm), 500-710 μm (yielding mean particle size of 605 μm) and a 1:1 (w/w) mix of those two fractions (yielding mean particle size 473 μm).

The formulations were produced by taking the fraction of the FCC/AcdiSol granules admixing the mouthfeel enhancers and compacting the mixture in to tablets such as described in the tablet preparation in the examples section.

Disintegration time was analyzed with Krüss Tensiometer K100 and the data was modeled according the following equation:

$$N(t) = \frac{(N(0)*k2 - 2N(0)*k1)*e^{-k2t}}{k2-k1} + \frac{N(0)*k1*e^{-k1t}}{k2-k1}$$

Where $N(0)$ is the netforce of the tablet ($N=mg-V\rho g$, m is the mass of the tablet, V is the volume of tablet, $\rho$ is the density of water and g is the acceleration of gravity) r(t) the mass of water uptake, k1 the weight gain rate constant and k2 the weight loss rate constant.

These equations describe the two simultaneous processes that take place during disintegration. The rate of water uptake, determined by k1 and the rate of mass loss determined by k2.

The results of fitting are shown in Table 3. High values of adjusted R2 are indicating adequacy of the selected model. According to the response surface analysis all factors (type of additive, amount of additive, particle size) were significant ($p<0.05$).

The mouthfeel was tested by an organoleptic panel and all the additives were enhancing the mouthfeel, showing no differences within the test set.

TABLE 3

| Formulation | k1 | k2 | Adj. $R^2$ | Disintegration time [sec] |
|---|---|---|---|---|
| G. arabicum, 5%, 340 µm | 0.8778 | 0.1366 | 0.9898 | 23.13 |
| G. arabicum, 10%, 340 µm | −0.0012 | 0.0750 | 0.9962 | 35.06 |
| G. arabicum, 5%, 605 µm | 2.4956 | 0.1150 | 0.9639 | 28.79 |
| G. arabicum, 10%, 605 µm | 10.6841 | 0.0813 | 0.9143 | 32.94 |
| G. arabicum, 7.5%, 473 µm | 319211 | 0.0823 | 0.9464 | 32.89 |
| HPC, 5%, 340 µm | 0.2979 | 0.2147 | 0.9790 | 18.17 |
| HPC, 10%, 340 µm | 1.6050 | 0.0599 | 0.9188 | 50.36 |
| HPC, 5%, 605 µm | 2.1074 | 0.0991 | 0.9579 | 30.48 |
| HPC, 10%, 605 µm | 2.3232 | 0.0685 | 0.9767 | 43.94 |
| HPC, 7.5%, 473 µm | 0.7174 | 0.0628 | 0.9251 | 48.45 |
| HPMC, 5%, 340 µm | 6.6276 | 0.0892 | 0.9796 | 31.94 |
| HPMC, 10%, 340 µm | 4.6939 | 0.0549 | 0.9317 | 50.59 |
| HPMC, 5%, 605 µm | 1.9736 | 0.0989 | 0.9685 | 31.34 |
| HPMC, 10%, 605 µm | 0.7105 | 0.1622 | 0.9854 | 19.79 |
| HPCM, 7.5%, 473 µm | 0.2053 | 0.1740 | 0.9864 | 24.85 |
| Instant gum, 5%, 340 µm | 3.2221 | 0.1808 | 0.9691 | 16.50 |
| Instant gum, 10%, 340 µm | 4.4210 | 0.1048 | 0.9867 | 27.82 |
| Instant gum, 5%, 605 µm | 2.0815 | 0.1703 | 0.9640 | 18.30 |
| Instant gum, 10%, 605 µm | 0.8205 | 0.1974 | 0.9075 | 16.31 |
| Instant gum, 7.5%, 473 µm | 0.2346 | 0.2129 | 0.9851 | 24.03 |
| PEO, 5%, 340 µm | 4.6163 | 0.0660 | 0.9639 | 46.70 |
| PEO, 10%, 340 µm | −0.0092 | 0.0323 | 0.9641 | 79.79 |
| PEO, 5%, 605 µm | 0.1782 | 0.1751 | 0.9828 | 38.11 |
| PEO, 10%, 605 µm | 1.3625 | 0.0963 | 0.9546 | 33.14 |
| PEO, 7.5%, 473 µm | 0.1447 | 0.0924 | 0.9384 | 39.26 |

FIG. 3: SEM pictures of FCC. Figures a) and b) show the surface of the granules, whereas Figure c) and d) show a cross-section through a FCC granule.

EXAMPLES

Materials and Methods

Functionalized calcium carbonate (FCC), Omya International AG, Switzerland) was used as a filler. Modified cellulose gum (Ac-Di-Sol®, FMC, USA) was used as a disintegrant. Magnesium stearate (Novartis, Switzerland) was used as a lubricant for tableting.

Methods

Roller Compaction and Milling

Before roller compaction, FCC was blended with 3% (w/w) of disintegrant. Therefore, FCC and the disintegrant were mixed for 10 min in a tumbling mixer (Turbula T2C, Willy A. Bachofen AG, Switzerland) at 32 rpm. Roller compaction was performed with a Fitzpatrick® Chilsonator IR220 roller compactor (The Fitzpatrick Company, USA) at a pressure of 10 bar. The feed rate and the roll speed were adjusted to obtain a ribbon thickness of 0.6 mm. The obtained ribbons were milled into granules with a FitzMill® L1A (The Fitzpatrick Company, USA) at 300 rpm.

Granule Analysis

A vibrating sieve tower was used to analyze the particle size distribution. 100 g of granules were put on steel wire screens (Vibro Retsch, Germany) with mesh sizes of 180 µm, 250 µm, 355 µm, 500 µm, and 710 µm and the sieving tower was shaken for 10 minutes at a shaking displacement of 1.5 mm. The amount of powder remaining on each sieve was weighted, whereas granules with a size of less than 180 µm or more than 710 µm were excluded for further processing.

Figure 1:
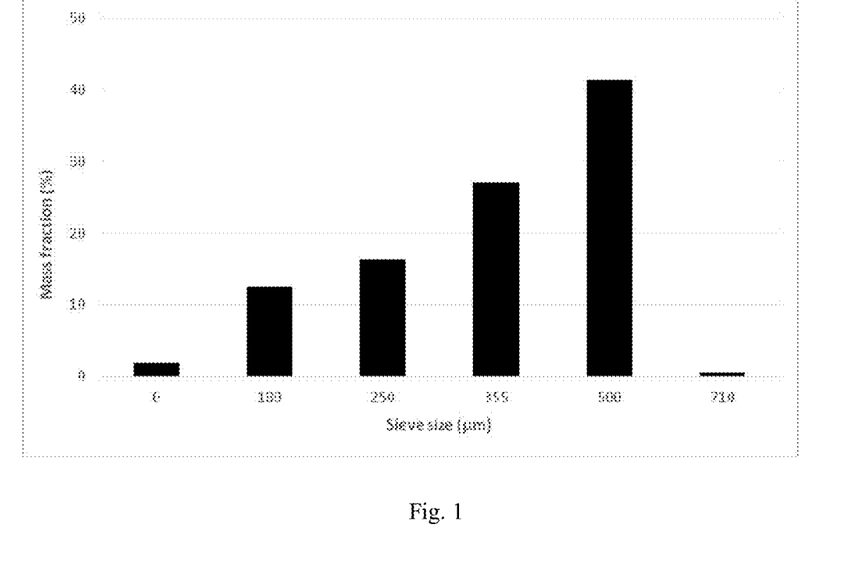
FIG. 1: Particle size distribution of granules after compaction and sieving
Figure 2:
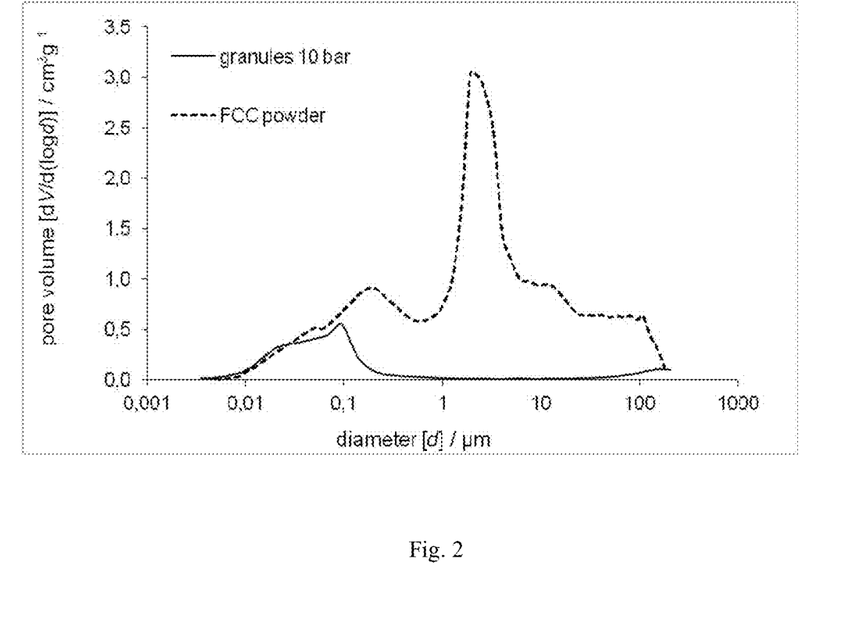
FIG. 2: shows a mercury porosimetry plot of the pore size distribution of FCC powder and roller compacted FCC granules. During the roller compaction process, FCC particles slipped closer together until the surfaces of different particles were in contact. This process of rearrangement and bonding during roller compaction is reflected in the porosimetry plot. Due to this densification of the powder bed, the high peak of FCC powder at a diameter of 1-10 µm was reduced dramatically and at the same time shifted to a smaller pore diameter. Nevertheless, the mercury porosimetry plot showed as well that the intraparticle structure of FCC can withstand the pressure during roller compaction and remains intact.
Figure 3:
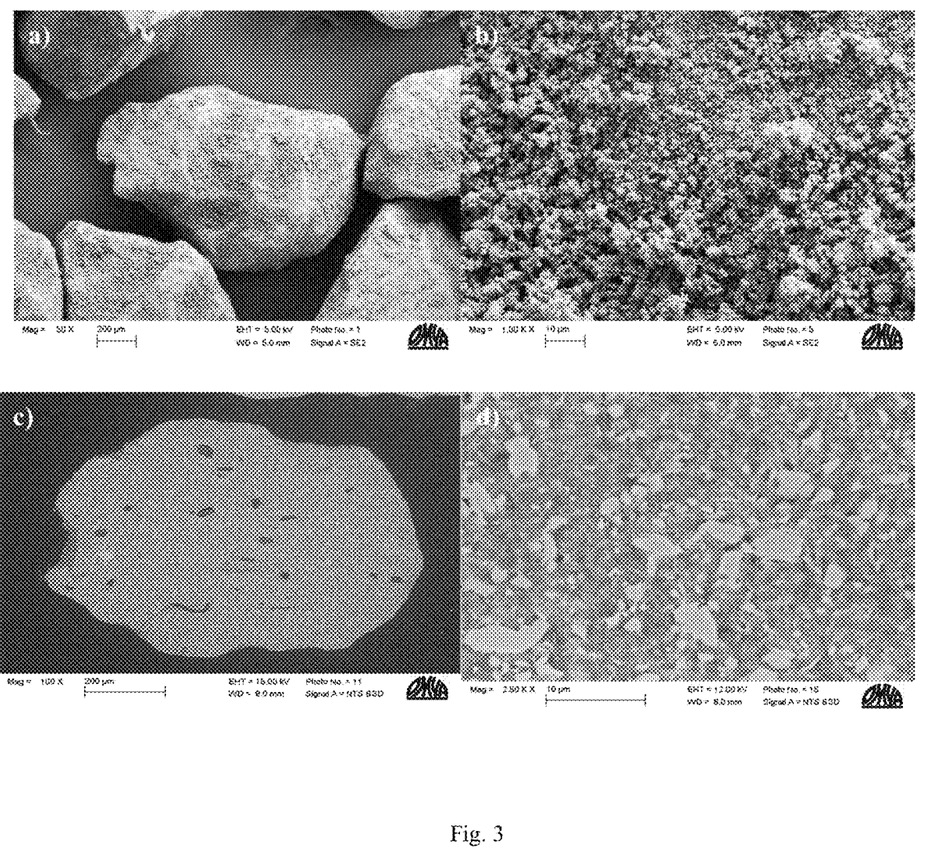

The particle size distribution of FCC granules with 3% (w/w) of disintegrant thus obtained showed that the mixture mainly contained coarse granules as shown in FIG. 1.

Flowability of selected granular fraction (from 180 µm to 710 µm) was measured according to European Pharmacopeia, $7^{th}$ Ed Strassbourg (France): Council of Europe 2011. A Mettler PM460 balance (Mettler Toledo, Switzerland) and a funnel with three different openings (5 mm, 7 mm, and 9 mm) were used to measure the flowability.

Loose Bulk Density 120 g of the granules of selected granular fraction (from 180 µm to 710 µm) were sieved through a 0.5 mm screen by means of a brush. 100±0.5 g of this sample were carefully filled through a powder funnel into the 250 mL measuring cylinder and the volume was read off to the nearest 1 mL. The loose bulk density was the calculated according the formula:

Loose bulk density [g/mL]=bulk volume [mL]/ weighed sample [g]

and the result was recorded to the nearest 0.01 g/mL.

BET Specific Surface Area of a Material

The BET specific surface area was measured via the BET process according to ISO 9277 using nitrogen, following conditioning of the sample by heating at 250° C. for a period of 30 minutes. Prior to such measurements, the sample was filtered, rinsed and dried at 110° C. in an oven for at least 12 hours.

Pore size distribution was measured with a Micromeritics Autopore V 9620 mercury porosimeter. This porosimeter has a maximum applied pressure of mercury 414 MPa (60,000 psia) which is equivalent to a pore diameter of 0.004 µm (~4 nm). Equilibration time used at each pressure was 20 seconds. This instrument can measure pore diameters over the 0.004 µm-1100 µm range.

Mercury porosimetry is based on the physical principle that a non-reactive, non-wetting liquid will not penetrate pores until sufficient pressure is applied to force its entrance. The relationship between the applied pressure and the pore size into which mercury will intrude is given by the Young-Laplace equation:

$$D = \frac{-4\gamma\cos\theta}{P}$$

where P is the applied pressure, D is the diameter, γ is the surface tension of mercury (480 dyne $cm^{-1}$ (0.48 $Nm^{-1}$)) and θ is the contact angle between mercury and the pore wall, usually taken to be 140°. The required pressure is inversely proportional to the size of the pores, only slight pressure being required to intrude mercury into large macropores, whereas much greater pressures are required to force mercury into micropores.

All results were corrected using the software Pore-Comp for mercury and penetrometer effects and also for sample skeletal compression (Gane, P. A. C., Kettle, J. P., Matthews, G. P. and Ridgway C. J. (1996): "Void space structure of compressible polymer spheres and consolidated calcium carbonate paper-coating formulations", Industrial & Engineering Chemistry Research Journal 35 (5), 1753-1764.)

Tablet Preparation

All granules with a size between 180 μm and 710 μm were used for tableting. Prior to the compaction, the granules were mixed in a tumbling mixer (Turbula T2C, Willy A. Bachofen AG, Switzerland) for 10 minutes at 32 rpm. The granules were compressed with a 11.28 mm round, flat tooling, using a Styl'One 105 mL tablet press (Medel'Pharm, France). The tablet press was instrumented with the Analis software version 2.01 (Medel'Pharm, France). A tablet with a weight of 500 mg and a hardness of 100 N was compacted out of the selected granule fraction. The resulting setting for the punch gap was kept constant over the whole compressive pressure range, ranging from 52 MPa to 116 MPa. Punches and die were manually lubricated with magnesium stearate.

Tablet Analysis (Weight, Diameter, Height, Crushing Force, Tensile Strength, and Disintegration)

Tablet weight, diameter, height, and crushing force were measured directly after tablet compression. Weight was determined with a Delta Range AX204 balance (Mettler Toledo, Switzerland). Diameter and height were measured with a micrometer screw of type CD-15CPX (Mitutoyo, Japan). Crushing forces were measured with a tablet hardness tester (8M, Dr. Schleuniger Pharmatron, Switzerland).

Tensile strength was calculated with equation (1):

$$\sigma_t = \frac{2*F}{\pi*d*h} \quad (1)$$

where $\sigma_t$ is the radial tensile strength (MPa), F is the crushing force (N), d is the tablet diameter (mm), and h is the tablet thickness (mm).

The disintegration and dispersion kinetics of the tablets were measured with a tensiometer (Krüss Processor Tensiometer K100MK2, Germany) according to the method described by Stimimann T, Maiuta N D, Gerard D E, Alles R, Huwyler J, Puchkov M. Functionalized Calcium Carbonate as a Novel Pharmaceutical Excipient for the Preparation of Orally Dispersible Tablets. Pharm Res. 1 Jul. 2013; 30(7):1915-25, or this study we used distilled water at room temperature as a dispersion media.

The invention claimed is:

1. A method for producing a dispersible dosage form, comprising the steps of:
    a) providing a functionalized calcium carbonate-comprising material, which is a reaction product of natural ground or precipitated calcium carbonate with carbon dioxide and one or more acids in an aqueous medium, wherein the carbon dioxide is formed in situ by the acid treatment and/or is supplied from an external source;
    b) providing at least one disintegrant;
    c) optionally providing at least one further formulating aid;
    d) mixing the functionalised calcium carbonate-comprising material of step a), the at least one disintegrant of step b) and the optionally at least one further formulating aid of step c);
    e) compacting the mixture obtained in step d) by means of a roller compactor at a compaction pressure in the range from 200 to 2000 kPa (2 to 20 bar) into a ribbon;
    f) milling the ribbon of step e) into granules; and
    g) sieving the granules of step f) by at least one mesh size;
    wherein the functionalised calcium carbonate-comprising material provided in step a) has an intra-particle intruded specific pore volume within the range of 0.15 to 1.35 cm$^3$/g, calculated according to the mercury intrusion porosimetry measurement.

2. The method of claim 1, further comprising a step b1) of providing at least one active ingredient or inactive precursor or both between step b), and step c) or step d).

3. The method of claim 1, further comprising a step d1) of providing at least one lubricant after step d) and mixing the mixture of step d) with the at least one lubricant of step d1) in a mixing step d2) prior to the compacting step e).

4. The method of claim 2, further comprising a step d1) of providing at least one lubricant after step d) and mixing the mixture of step d) with the at least one lubricant of step d1) in a mixing step d2) prior to the compacting step e).

5. The method of claim 1, further comprising a step h) of providing at least one active ingredient and/or inactive precursor and optionally a step i) of providing further additives, and mixing the granules of step f) with the at least one active ingredient and/or inactive precursor of step g) and the optionally provided further additives of step h).

6. The method of claim 1, further comprising a final step j) of tableting the material obtained in the last step.

7. The method according to claim 1, wherein the natural ground calcium carbonate is selected from calcium carbonate comprising minerals selected from the group consisting of marble, chalk, limestone, dolomite and any mixture thereof; and the precipitated calcium carbonate is selected from the group of precipitated calcium carbonate having aragonitic, vateritic, or calcitic mineralogical crystal forms, and any mixture thereof.

8. The method of claim 1, wherein the functionalized calcium carbonate-comprising material is a reaction product of natural ground calcium carbonate with carbon dioxide and phosphoric acid in an aqueous medium, wherein the carbon dioxide is formed in situ by the acid treatment and/or is supplied from an external source.

9. The method according to claim 1, wherein the functionalised calcium carbonate-comprising material has a BET specific surface area of from 20 m$^2$/g to 450 m$^2$/g, measured using the nitrogen and BET method according to ISO 9277.

10. The method of claim 1, wherein the functionalised calcium carbonate-comprising material has a BET specific surface area of from 20 m$^2$/g to 140 m$^2$/g, measured using the nitrogen and BET method according to ISO 9277.

11. The method of claim 1, wherein the functionalised calcium carbonate-comprising material comprises particles having a volume median grain diameter $d_{50}$ of from 2 μm to 50 μm.

12. The method according to claim 1, wherein the functionalised calcium carbonate-comprising material comprises particles having a volume median grain diameter $d_{50}$ of from 1 μm to 35 μm.

13. The method according to claim 1, wherein the functionalised calcium carbonate-comprising material has an intra-particle intruded specific pore volume within the range of 0.30 to 1.30 cm$^3$/g, calculated according to the mercury intrusion porosimetry measurement.

14. The method according to claim 1, wherein the functionalised calcium carbonate-comprising material has an intra-particle intruded specific pore volume within the range of 0.40 to 1.25 cm$^3$/g, calculated according to the mercury intrusion porosimetry, measurement.

15. The method according to claim 1, wherein the granules have a flowability from 1.36 g/s to 5.75 g/s when compacted at 1000 kPa (10 bar) and sieved with mesh sizes of 180 µm, 250 µm, 355 µm, 500 µm, and 710 µm, and the granules with size less than 180 µm and more than 710 µm were excluded, when measured according to European Pharmacopeia, 7$^{th}$ Ed Strassbourg (France): Council of Europe 2011, at an opening diameter from 5 min to 9 mm.

16. The method according to claim 1, wherein the granules have a loose bulk density of 0.65 g/cm$^3$ when compacted at 1000 kPa (10 bar) and sieved with mesh sizes of 180 µm, 250 µm, 355 µm, 500 µm, and 710 µm, and the granules with size less than 180 µm and more than 710 µm were excluded.

17. The method according to claim 1, wherein the at least one disintegrant is selected form the group consisting of modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-, hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxypropyl methyl cellulose phthalate, shellac, and any mixture thereof.

18. The method according to claim 1, wherein the at least one disintegrant is a modified cellulose gum.

19. The method according to claim 1, wherein the at least formulating aid is at least one inner-phase lubricant and/or outer-phase lubricant; and is provided in a total amount from 0.1 wt.-% to 10.0 wt.-%, based on the total weight of the functionalized calcium carbonate-comprising material of step a).

20. The method according to claim 1, wherein the at least formulating aid is at least one inner-phase lubricant and/or outer-phase lubricant; and is provided in a total amount from 0.3 wt.-% to 5.0 wt.-%, based on the total weight of the functionalized calcium carbonate-comprising material of step a).

* * * * *

UNITED STATES PATENT AND TRADEMARK OFFICE
CERTIFICATE OF CORRECTION

PATENT NO. : 10,617,648 B2
APPLICATION NO. : 15/554235
DATED : April 14, 2020
INVENTOR(S) : Wagner-Hattier et al.

It is certified that error appears in the above-identified patent and that said Letters Patent is hereby corrected as shown below:

On the Title Page

Item [73], delete "Blue Ash, OH (US)" and insert --Oftringen (CH)-- therefor

Signed and Sealed this
Fifteenth Day of November, 2022

Katherine Kelly Vidal
*Director of the United States Patent and Trademark Office*